(12) United States Patent
Haberlin et al.

(10) Patent No.: US 11,299,570 B2
(45) Date of Patent: Apr. 12, 2022

(54) LOW-VISCOSITY PHOTOCURABLE ADHESIVE COMPOSITIONS

(71) Applicant: HENKEL IP & HOLDING GMBH, Duesseldorf (DE)

(72) Inventors: Gavin Haberlin, County Dublin (IE); Darragh Fitzpatrick, County Kildare (IE); Martin Smyth, County Dublin (IE); Lisa Kennedy, County Meath (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 128 days.

(21) Appl. No.: 16/680,826

(22) Filed: Nov. 12, 2019

(65) Prior Publication Data

US 2020/0079949 A1 Mar. 12, 2020

Related U.S. Application Data

(63) Continuation of application No. PCT/EP2018/062175, filed on May 10, 2018.

(30) Foreign Application Priority Data

May 23, 2017 (GB) ..................................... 1708258

(51) Int. Cl.
*C08F 220/18* (2006.01)
*C08K 5/00* (2006.01)
(Continued)

(52) U.S. Cl.
CPC ...... *C08F 220/1811* (2020.02); *C08K 5/0041* (2013.01); *C08K 5/45* (2013.01);
(Continued)

(58) Field of Classification Search
CPC ... A61M 339/00; C08F 220/00; C08F 220/18; C08F 220/1181; C08F 220/28;
(Continued)

(56) References Cited

U.S. PATENT DOCUMENTS 5,624,759 A 4/1997 Usifer et al.
6,080,450 A 6/2000 Cantor
(Continued)

FOREIGN PATENT DOCUMENTS

CA 2170118 A1 6/1997
CN 101586011 11/2009
(Continued)

*Primary Examiner* — Sanza L. McClendon
(74) *Attorney, Agent, or Firm* — Steven C. Bauman

(57) ABSTRACT

Photocurable (meth)acrylate compositions with low viscosity when uncured, and high flexibility and shear/tensile strength when cured, further possessing rapid tack-free fixture times, comprising mixtures of urethane acrylate resin, isobornyl acrylate, N,N-dimethylacrylamide, a photoinitiator component, and a low percentage of tetrahydrofurfuryl acrylate, for example from about 9% to about 15% by weight based on the weight of the composition. Applications can include adhesive bonding of medical tubing, UV/Visible transparent plastics material medical devices or equipment, or other flexible UV/Visible transparent material substrates.

29 Claims, 12 Drawing Sheets

(51) Int. Cl.
*C08K 5/45* (2006.01)
*C08K 5/53* (2006.01)
*C08L 33/10* (2006.01)
*C08L 33/26* (2006.01)
*C08L 37/00* (2006.01)
*C08L 75/04* (2006.01)
*C08L 83/06* (2006.01)
*C09J 5/00* (2006.01)
*A61M 39/00* (2006.01)
*C08F 220/28* (2006.01)

(52) U.S. Cl.
CPC ................ *C08K 5/53* (2013.01); *C08L 33/10* (2013.01); *C08L 33/26* (2013.01); *C08L 37/00* (2013.01); *C08L 75/04* (2013.01); *C08L 83/06* (2013.01); *C09J 5/00* (2013.01); *A61M 39/00* (2013.01); *C08F 220/281* (2020.02); *C08L 2205/035* (2013.01); *C08L 2312/06* (2013.01); *C09J 2301/416* (2020.08)

(58) Field of Classification Search
CPC .............. C08F 220/282; C08F 220/343; C08F 220/56; C08K 5/0041; C08K 5/45; C08K 5/53; C08L 33/10; C08L 33/26; C08L 37/00; C08L 75/04; C08L 83/06; C08L 2205/035; C08L 2312/06; C09J 4/00; C09J 4/06; C09J 5/00; C09J 2301/416

USPC ........................... 522/113, 116, 120, 121, 96
See application file for complete search history.

(56) References Cited

U.S. PATENT DOCUMENTS

| | | | |
|---|---|---|---|
| 8,247,509 | B2 | 8/2012 | Okamoto et al. |
| 9,718,975 | B2 * | 8/2017 | Nerad ................... C09D 11/30 |
| 2015/0083317 | A1 | 3/2015 | Zhang et al. |
| 2015/0166860 | A1 | 6/2015 | Yuan et al. |
| 2015/0252202 | A1* | 9/2015 | Nerad .................. C09D 11/322 |
| | | | 522/26 |

FOREIGN PATENT DOCUMENTS

| | | | |
|---|---|---|---|
| CN | 103305132 | B | 3/2015 |
| CN | 104694057 | A | 6/2015 |
| GB | 2406572 | A | 4/2005 |
| JP | 2013241508 | | 12/2013 |
| JP | 2015120781 | | 7/2015 |
| KR | 20160028137 | A * | 3/2016 |
| WO | 200845517 | A2 | 4/2008 |
| WO | 2013013590 | A1 | 1/2013 |
| WO | 2014129819 | A1 | 8/2014 |
| WO | 2014193903 | A3 | 12/2014 |
| WO | 2016008130 | A1 | 1/2016 |

* cited by examiner

LOW-VISCOSITY PHOTOCURABLE ADHESIVE COMPOSITIONS

FIELD

The present invention relates to a photocurable acrylic adhesive composition of a type which can be applied to an article in a low viscosity uncured form for example as a coating.

BRIEF DESCRIPTION OF RELATED TECHNOLOGY

Low viscosity photocurable acrylic adhesives with good tack-free cure times, good fixture times, and good tensile strengths are known. However, adhesive compositions which exhibit these properties and additionally exhibit good flexibility in the cured product, remain highly desirable.

For example it is desirable to provide a composition that has desirable properties in the cured product as measured by elongation-at-break.

U.S. Pat. No. 6,080,450 discloses use of a phosphine oxide photoinitiator that enables the effective curing of a polymerizable acrylate formulation despite the incorporation of a high concentration of a fluorescing agent, thereby facilitating, and enhancing, the efficiency of evaluation of the cured deposit utilizing its fluorescent response. The enhanced fluorescence of the formulation in U.S. Pat. No. 6,080,450 is directed to use in coatings and inks that exhibit increased levels of response to scanner beams, for example for non-destructive inspection.

Notwithstanding this and other known compositions it is still desirable to provide alternative compositions that exhibit desirable properties both in the uncured composition and in the cured composition.

SUMMARY

In one aspect, the present invention provides a photocurable (meth)acrylate composition comprising tetrahydrofurfuryl acrylate, urethane acrylate resin, isobornyl acrylate, N,N-dimethylacrylamide and a photoinitiator component, as described herein, and also as set out in the claims.

The present invention thus provides a photocurable acrylic adhesive composition that exhibits low viscosity (in the uncured state) and that exhibits high flexibility, and high elongation-at-break properties once cured. The composition of the invention also exhibits tack-free surface properties. Cure speed properties are good. Bond strengths are good also.

In another aspect, the present invention provides a method of curing said photocurable (meth)acrylate composition, comprising the steps of (i) applying a claimed composition to at least a first substrate and (ii) exposing the composition to radiation from a light-emitting diode (LED), or other radiation source, or other actinic radiation source, electron beam (e-beam), or mercury arc, so as to cure the composition of the invention. Actinic radiation can comprise, for example, ultraviolet (UV) radiation, for example, UV-A radiation, for example UV-A radiation at 365 nm.

As an example, at least one application of such a composition would be in bonding plastic medical tubing to plastic medical bags, such as those used for intravenous therapy, or bonding tubing such as that used for insulin pumps to other plastics substrates. Thus, a problem to be solved is the identification of compositions enabling a low viscosity photocurable acrylic adhesive with high flexibility—that is, with high elongation-at-break once cured—while also possessing good tack-free time, good fixture time and good strength once cured.

It was surprisingly found that the addition of tetrahydrofurfuryl acrylate, in the range from 9% to 15% by weight, based on the total weight of the composition, to formulations containing a blend of urethane acrylate resin, isobornyl acrylate and N,N-dimethylacrylamide which already possessed good fixture time and good tack-free, conferred on the resulting composition the ability to also achieve the desired high flexibility and high elongation-at-break properties when cured. Thus, such compositions provide additional desired properties.

The present invention provides a photocurable (meth) acrylate composition having a viscosity at 25° C. of less than about 550 mPa·s, such as less than about 500 mPa·s, typically less than about 450 mPa·s, including less than about 400 mPa·s, suitably less than about 350 mPa·s, optionally less than about 300 mPa·s, for example less than about 250 mPa·s, and desirably less than about 200 mPa·s.

The present invention provides a photocurable (meth) acrylate composition, wherein the photocured (meth) acrylate composition has an elongation-at-break value of greater than 130%, such as greater than 135%, for example greater than 140%, including greater than 145%, suitably greater than 150%.

The present invention provides a photocurable (meth) acrylate composition, wherein the (meth) acrylate composition when photocured has a shear strength as determined by ISO 4587 of greater than about 4 N/mm$^2$, such as greater than about 5 N/mm$^2$, for example greater than about 10 N/mm$^2$, desirably greater than about 15 N/mm$^2$.

The combination of tetrahydrofurfuryl acrylate, urethane acrylate resin, isobornyl acrylate and N,N-dimethylacrylamide confers tack-free cure at low actinic radiation intensity. The uncured composition of urethane acrylate resin, isobornyl acrylate, tetrahydrofurfuryl acrylate and N,N-dimethylacrylamide initially has low viscosity, but still cures in an acceptable time with good cure speed, good tack-free cure, high bond strength and high flexibility.

The flexibility in the cured material facilitates bond interface mobility. The benefit of this characteristic, for example in medical device applications, is realised where movement such as flexing of the apparatus occurs. Such applications can include at least the bonding of medical grade plastics such as tubing to other substrates.

The components of the claimed compositions-including at least tetrahydrofurfuryl acrylate, urethane acrylate resin, isobornyl acrylate, N,N-dimethylacrylamide and a photoinitiator component—are mixed together. This composition may be cured, when desired, by actinic radiation. Compositions of the invention can thus be photocured. The compositions of the invention can be cured by any suitable actinic radiation.

The following commercially available photocurable adhesive compositions were used in comparative tests with the newly invented compositions disclosed herein: Loctite 3341 (hereinafter, "3341"), Loctite 3933 (hereinafter, "3933"), Dymax 1405-M-UR-SC (hereinafter, "1405-M-UR-SC"), Dymax 1191-M (hereinafter, "1191-M"). 'Locitite' and 'Dymax' are registered trademarks.

LED Tack-Free Cure at Low Actinic Radiation Intensity:

As used herein the term "tack-free" refers to a property of a cured composition. A tack-free composition is a composition with a surface that is not sticky/tacky when touched once cured. Accordingly, a tack-free composition is one that will not be tacky towards the surfaces which it will typically come in contact with (for example packaging, for example operators hands etc.) and which will not transfer material to such surfaces; thus such compositions are non-tacky and are termed tack-free. Tackiness of cured compositions was assessed by placing talcum powder on a cured sample and examining the cure time of the composition required (in seconds) to allow removal of the talc to give a clear surface. Samples from which the talc could not be readily removed were considered tacky, and not "tack-free". Samples from which talc could be readily removed to give a clear surface were considered to be tack-free. A cured composition was considered to have a tack-free surface when talcum powder could be removed without altering the appearance of the adhesive surface or causing the surface to become dull.

For compositions of the present invention, tack-free surface cure is achieved in less than 40 seconds, such as less than 35 seconds, typically less than or equal to 30 seconds, for example at an intensity less than 0.5 W using LED light sources which have capacity to reach intensities up to 10 W of monochromatic irradiance. Such monochromatic light can comprise wavelengths of, for example, from 365 nm to 405 nm.

Low Viscosity:

Low viscosity, as used in relation to the present invention refers to viscosity values of less than about 550 mPa·s, as measured for uncured compositions at 25° C. Low viscosity material properties of uncured compositions when combined with high elongation-at-break performance of the cured material is a combination of properties that is desirable and these properties are achieved with compositions of the invention.

Cure Speed:

Fixture times, measured using glass microscope slides, of less than 1 second are obtained. Such rapid fixture times may be achieved even at low light intensity exposures for example 10 mW for 405 nm or 365 nm LED light.

High Strength Bonding Performance:

Increased bond strength across a range of application specific polymers has been obtained. High bond strength is seen for thermoplastic polyurethane and polycarbonate bonding using the compositions of the invention, demonstrating a significant improvement over prior art. High bond strength to polyvinylchloride is also seen using the compositions of the invention.

High Flexibility:

High elongation-at-break (greater than 130%, such as greater than 150%) of acrylic polymers is typically achieved by using long chain polyurethanes or an elastomer component. The compositions of the current invention, once cured, are flexible and achieve greater than 130% elongation, typically greater than 150% elongation before breaking. And this is achieved by curing a composition that has a low viscosity.

Tetrahydrofurfuryl acrylate is a widely known bonding promoter; however, the currently claimed invention is specifically directed to photocurable compositions with increased elongation-at-break and/or increased flexibility, achieved when tetrahydrofurfuryl acrylate is used in combination with urethane acrylate resin, isobornyl acrylate and N,N-dimethylacrylamide. The low viscosity of the resulting compositions, prior to curing, has significant relevance for applications; it facilitates, for example, use with low gap/tight fitting for example for tube-fitting for example to medical devices.

Compositions of the invention can be cured by actinic radiation which passes through at least one substrate that is bonded to another substrate. In such a case the substrate is sufficiently transmissive to incident actinic radiation. Desirably both substrates are sufficiently transmissive to incident actinic radiation. In this way assembly of substrates can take place with a composition of the invention in place, and, after assembly, photocuring can be effected by actinic radiation. Even though a substantial proportion of the irradiation may be incident on a substrate it will still transmit to the composition of the invention to effect cure. This means that even where a composition in place for bonding is shielded between the substrates, effective cure can occur by transmission of the actinic radiation through the substrate(s). Or put another way, even if none, or only a small proportion of the composition can be directly exposed to the actinic radiation, with the remainder shielded by the substrate(s), cure can still be effected by indirect exposure by actinic radiation transmitted through the substrates.

Such properties are desirable, for example where there are tubes which are often fitted into a lumen in another substrate. Because such tubes are often for carrying fluids, and it is desirable to have a fluid tight or non-leaking joints, there is often a tight fit (for example an interference fit) when one is joined to the other. A composition of the invention can be utilised to bond the two substrates together, such as to fix a tube within a lumen. Its low viscosity allows it to be easily placed within a tight space between two substrates. And the composition can be photocured, by transmission of actinic radiation through one or both substrates. And once cured, it forms a flexible bond that can sustain its bond strength, even when exposed to typical movement forces. Furthermore the bond strength itself is very good.

It will be appreciated that the low viscosity of the composition of the invention allows it to be easily placed between and/or flow between tight fitting substrates. Upon cure there is good tack-free properties meaning the assembled substrates can be handled. Upon cure there is very good bond strength. Furthermore the bond is not hard/brittle and has sufficient flexibility to allow movement without cracking or disintegrating. The bond formed is thus non-friable; it is flexible.

BRIEF DESCRIPTION OF THE DRAWINGS

Embodiments of the invention will be described, by way of example only, with reference to the accompanying drawings in which.

Figure 1:
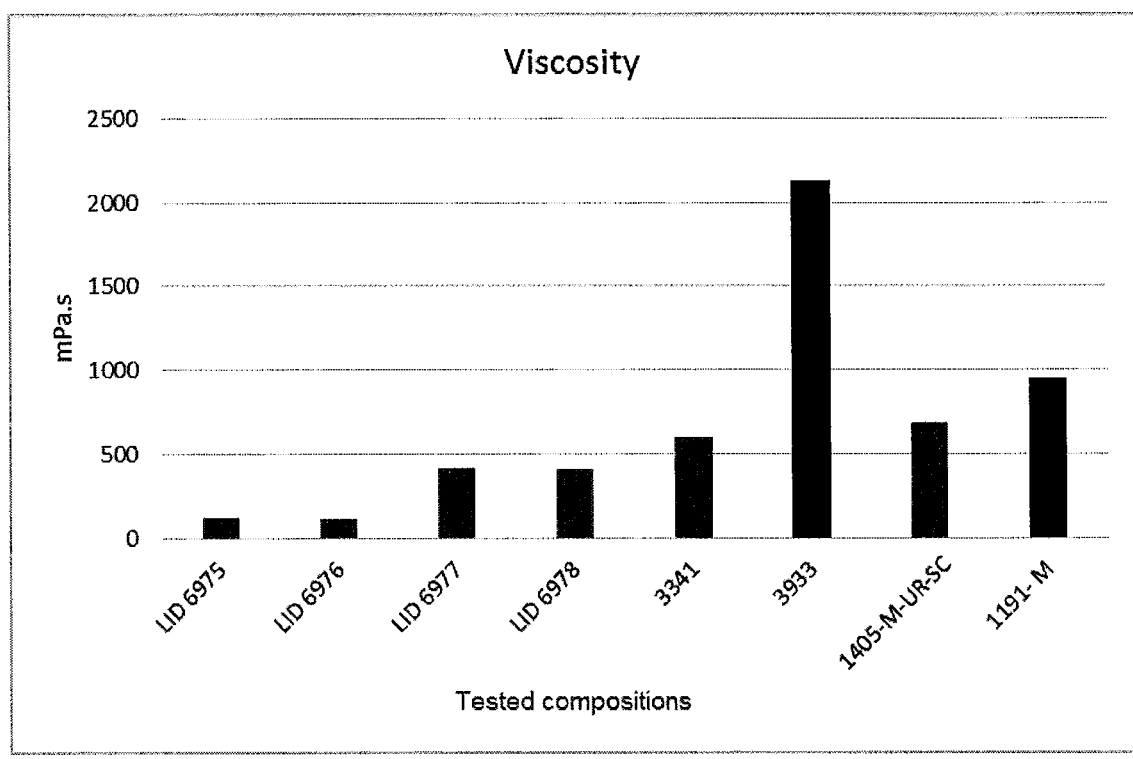
FIG. 1 is a bar chart depicting the viscosity of uncured tested compositions at 25° C. These include compositions claimed by the current invention (LID6975, LID6976, LID6977, LID6978) and prior-art compositions (3341, 3933, 1405-M-UR-SC, 1191-M). All of the compositions of the invention exhibit a viscosity below 550 mPa·s.

In the Figures, grey bars are indicative of performance that meets or improves on the targeted composition performance (as set forth in Table 1), while black bars indicate compositions that failed to meet the targeted performance.

While certain comparative compositions may exhibit some desirable properties it is the set of properties in combination exhibited by compositions of the present invention that set them apart.

DETAILED DESCRIPTION

The present invention provides, in one aspect, photocurable (meth)acrylate compositions wherein tetrahydrofurfuryl acrylate is present in an amount from about 5% to about 30%, such as from about 7% to about 18%, for example from about 9% to about 15% by weight based on the weight of the composition. It was surprisingly found that inclusion of tetrahydrofurfuryl acrylate in such small proportions was sufficient to confer the desired properties on the resulting compositions; namely low viscosity prior to photocuring, and combined high flexibility and strength once cured, while also fixing rapidly upon exposure to suitable sources of actinic radiation to produce tack-free surfaces once cured.

The urethane acrylate resin, that is a component of the photocurable (meth)acrylate compositions that are the subject of the present invention, comprises oligomers having a number average molecular weight of from about 500 to about 100000, and/or having a mass average molar mass ($M_w$) of about 21000. The number average molecular weight and the $M_w$ of a urethane acrylate resin can be measured for example by gel permeation chromatography. In one aspect, the photocurable (meth)acrylate compositions provided by the present invention have urethane acrylate resin present in an amount from about 18% to about 45%, such as from about 20% to about 40%, for example from about 26% to about 38% by weight based on the total weight of the composition.

In one aspect, the photocurable (meth)acrylate compositions provided by the present invention have isobornyl acrylate present in an amount from about 15% to about 32%, such as from about 20% to about 30%, for example from about 23% to about 28% by weight based on the total weight of the composition. For the purposes of formulation, isobornyl acrylate and urethane acrylate resin can be optionally added in combination during the formulation process.

In one aspect, the photocurable (meth)acrylate compositions provided by the present invention have N,N-dimethylacrylamide present in an amount from about 18% to about 30%, such as from about 20% to about 25%, for example from about 24% to about 24.5% by weight based on the total weight of the composition.

The photocurable (meth)acrylate compositions provided by the present invention can further comprise an epoxide-bearing organosilane, wherein the epoxide-bearing organosilane is present in an amount from about 0.2% to about 2%, such as from about 0.5% to about 1.5%, for example from about 0.9% to about 1.1% by weight based on the total weight of the composition. By way of non-limiting example, such an epoxide-bearing organosilane can be 3-glycidoxypropyltrimethoxysilane.

The photoinitiator component may be selected from at least one of ethyl(2,4,6-trimethylbenzoyl) phenylphosphinate, 1-hydroxycyclohexylphenylketone, (2,4,6-trimethylbenzoyl) diphenylphosphineoxide, oxy-phenyl-acetic acid 2-[2 oxo-2-phenyl-acetoxy-ethoxy]-ethyl ester, oxy-phenyl-acetic 2-[2-hydroxy-ethoxy]-ethyl ester, 2-hydroxy-2-methyl-1-phenyl-1-propanone, phosphine oxide phenyl bis (2,4,6-trimethyl benzoyl), iodonium (4-methylphenyl)[4-(2-methylpropyl) phenyl]-hexafluorophosphate(1-), or combinations thereof.

In one aspect, the inventive photocurable (meth)acrylate compositions have a photoinititator component present in an amount from about 0.01% to about 6%, such as from about 0.5% to about 5%, for example from about 0.8% to about 4.8% by weight based on the total weight of the composition.

In another aspect, the present invention provides photocurable (meth)acrylate compositions wherein the compositions further comprises a fluorescent agent, wherein the fluorescent agent is present from about 0.005% to about 0.5%, such from about 0.02% to about 0.15%, for example from about 0.08% to about 0.12% by weight based on the total weight of the composition. Such a fluorescent agent can be useful to help to identify regions that have been treated with the composition. Advantageously, compositions comprising at least one fluorescent agent can for example help to identify presence of the composition. For example flexible parts, such as parts useful in the assembly of medical equipment like tube sets and needle assemblies, that have been treated with the adhesive compositions of the present invention, can then benefit from a positive fluorescence signal indicating the presence of the adhesive composition on the part to be assembled. A further advantage of compositions comprising at least one fluorescent agent is, for example, that fluorescence of the fluorescent agent can be used for quality control purposes, for example during manufacture of medical parts on an assembly line, for example for determination that a correct amount of adhesive has been applied and/or is present in the final product. Any suitable fluorescent agent may be used, such as those well known in the art. By way of example, one such useful fluorescent agent is 2,5-thiophenediylbis(5-tert-butyl-1,3-benzoaole). Another is available commercially from Angstrom Technologies (Angstrom Technologies, Inc., 7880 Foundation Drive, Florence, Ky. 41042, USA) under the trade name "Scanning Compound #25" (SC-25, hereinafter referred to as Natmar Scanning 25). "Scanning Compound #25" is a registered trademark. Natmar Scanning 25 is a synthetic organic molecule that has a fluorescent agent with a fluorescence emission range from about 615 nanometres (nm) to about 640 nm.

In one aspect the current invention provides a method of curing the claimed compositions comprising the steps of applying the claimed compositions to at least a first substrate and exposing the composition to radiation or other actinic radiation so as to cure the composition. By way of example, the source of actinic radiation can comprise an LED source. By way of further example the source of actinic radiation can comprise LEDs, e-beams, or mercury arc sources. In one embodiment, the at least one substrate can comprise a flexible UV transparent part.

In a further embodiment, the at least one substrate can comprise a plastics material, wherein at least one of the plastics material substrates is transparent to UV or visible light. By way of example and with no intention to limit the invention, the plastics material, which is desirably transparent to actinic radiation, can be selected from at least one of polyvinyl chloride, polyethylene, polypropylene, polycarbonate, acrylonitrile butadiene styrene, polyethylene terephthalate and thermoplastic elastomers.

At least one of the first substrate and the second substrate to be bonded using a composition of the invention can comprise tubing:
(i) for the transfer, including drainage, of medical fluids including liquids such as electrolyte e.g. saline or blood and gases such as oxygen;
(ii) in a form which is inserted into the body, such as a catheter, for example for insertion within the vasculature, or for insertion within a tract such as a urinary tract;
(iii) part of an implantable device;
(iv) for connecting to a cannula which is for insertion into a subject for example an intravenous catheter;
(v) for connecting to a medical device such as a pump, including insulin pumps, or haemodialysis equipment;
(vi) for use as a sheath, for example to house wires, for example to house wires from medical equipment.

Comparison of Compositions with and without Tetrahydrofurfuryl Acrylate:

The presence of the tetrahydrofurfuryl acrylate component of the composition is a factor in achieving the desired properties. This was confirmed in part by comparing the following two compositions, that differ in that one (TB8) contains tetrahydrofurfuryl acrylate and the other (TB3) does not.

Composition TB3 (containing no tetrahydrofurfuryl acrylate): 27.60% urethane acrylate resin, 43.38% isobornyl acrylate, 25% dimethylacrylamide, 4% ethyl (2,4,6-trimethylbenzoyl) phenylphosphinate, 0.02% 2,5-thiophenediylbis(5-tert-butyl-1,3-benzoxazole); wherein the percentages are by weight based on the total weight of the composition.

Composition TB8 (containing tetrahydrofurfuryl acrylate): 15% tetrahydrofurfuryl acrylate, 27.60% urethane acrylate resin, 28.38% isobornyl acrylate, 25% dimethylacrylamide, 4% ethyl (2,4,6-trimethylbenzoyl) phenylphosphinate, 0.02% 2,5-thiophenediylbis(5-tert-butyl-1,3-benzoxazole); wherein the percentages are by weight based on the total weight of the composition.

Results of Comparison:

The composition containing tetrahydrofurfuryl acrylate, TB8, exhibited an elongation at break value of 151.5%. In contrast, the composition lacking tetrahydrofurfuryl acrylate, TB3, exhibited an elongation at break value of only 5.6%. TB8 also possessed stronger bonding on plastics, including polycarbonate and polypropylene, and possessed a lower viscosity than TB3.

This result emphasises the importance of tetrahydrofurfuryl acrylate to the compositions claimed in the current invention, since in the absence of tetrahydrofurfuryl acrylate the composition TB3 did not exhibit the desirable properties; the comparison particularly highlights the striking improvement in elongation properties conferred by the inclusion of tetrahydrofurfuryl acrylate

EXAMPLES

LID6975

LID6975 is a composition of the invention exhibiting desirable properties as set out herein. LID6975 comprises 15% tetrahydrofurfuryl acrylate, 26.75% urethane acrylate resin, 27.85% isobornyl acrylate, 24.5% dimethylacrylamide, 1% 3-(glycidoxypropyl)trimethoxysilane, 4% ethyl (2,4,6-trimethylbenzoyl) phenylphosphinate, 0.8% 1-hydroxycyclohexyl phenyl ketone, and 0.1% 2,5-thiophenediylbis(5-tert-butyl-1,3-benzoxazole), wherein the percentages are by weight based on the total weight of the composition.

LID6976

LID6976 is a composition of the invention exhibiting desirable properties as set out herein. The composition of LID6976 matches that of LID6975, except that 2,5-thiophenediylbis(5-tert-butyl-1,3-benzoxazole) is replaced with Natmar Scanning 25 at the same weight percent.

LID6977

LID6977 is a composition of the invention exhibiting desirable properties as set out herein. LID6977 comprises 9% tetrahydrofurfuryl acrylate, 37.69% urethane acrylate resin, 23.41% isobornyl acrylate, 24% dimethylacrylamide, 1% 3-(glycidoxypropyl)trimethoxysilane, 4% ethyl (2,4,6-trimethylbenzoyl) phenylphosphinate, 0.8% 1-hydroxycyclohexyl phenyl ketone, and 0.1% 2,5-thiophenediylbis(5-tert-butyl-1,3-benzoxazole), wherein the percentages are by weight based on the total weight of the composition.

LID6978

LID6978 is a composition of the invention exhibiting desirable properties as set out herein. The composition of LID6978 matches that of LID6977, except that 2,5-thiophenediylbis(5-tert-butyl-1,3-benzoxazole) is replaced with Natmar Scanning 25 at the same weight percent.

A range of plastic medical tubing samples were bonded using the composition claimed in the current invention. These were then placed under tension. In all cases, there was substrate-failure, which is indicative of the exceptionally strong bond strength.

Viscosity Test:

Viscosity was a measured at 25° C. using a Haake rotoviscometer PK100, M10/PK1 2° Cone and Plate system at a shear rate of 200 $s^{-1}$. Results are depicted in FIG. 1.

Figure 2:
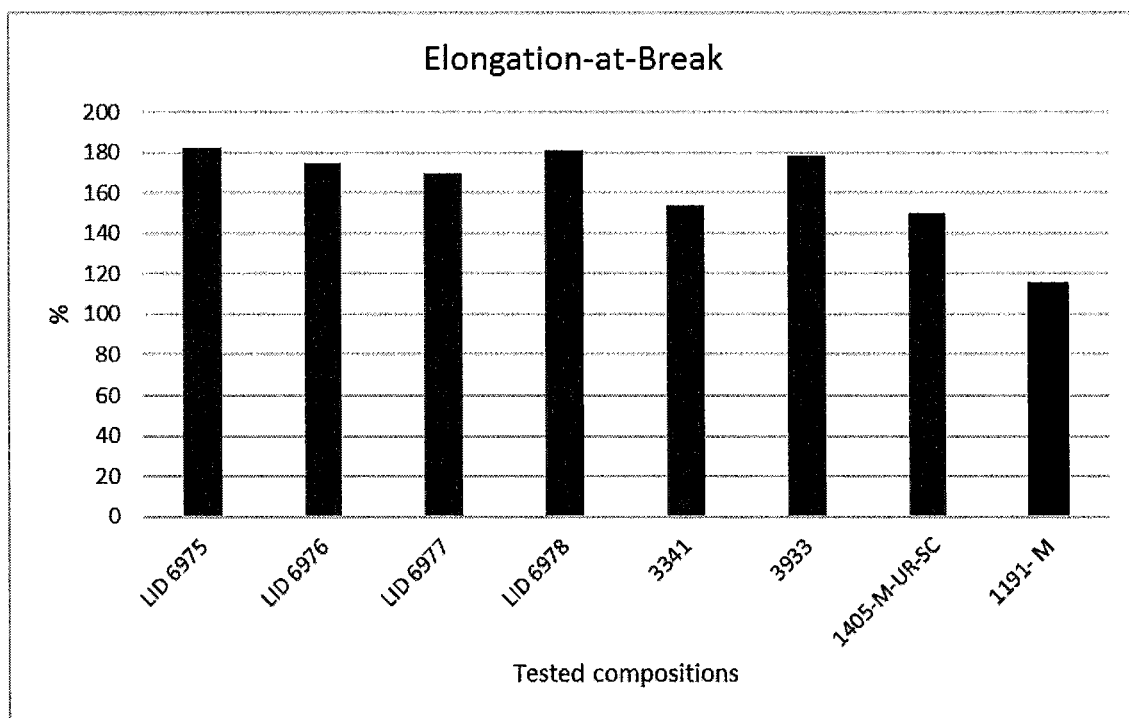
FIG. 2 is a bar chart depicting the elongation-at-break values (%) of tested cured compositions. All of the compositions of the invention tested exhibit high elongation-at-break values, for instance, greater than 150%. Comparative composition 3933 also has an elongation-at-break greater than 150%, however it has a viscosity at 25° C. of over 2000 mPa·s (see FIG. 1).

Flexibility Test; Measuring Elongation-at-Break:

To measure the percentage elongation-at-break of cured compositions, which is a measure of flexibility, film samples were prepared by drawing the uncured compositions to a thickness of approximately 1 mm (approximately 0.039 inches) using a stainless steel drawdown applicator (BYK-Gardner) on a polytetrafluoroethylene plate. The film was then photocured by UV-A radiation (50 mW/cm$^2$) and dogbone shape samples were cut from the film in accordance with ASTM D638, Type IV. The samples were tested on a Sintech 1-D Instron machine (MTS Sintech) by pulling at 30.48 cm/min (12 inches/min), with the initial distance between the grips set at 6.35 cm (2.5 inches). Percentage elongation values at break were recorded for each cured composition sample film and are reported in FIG. 2.

Figure 3:
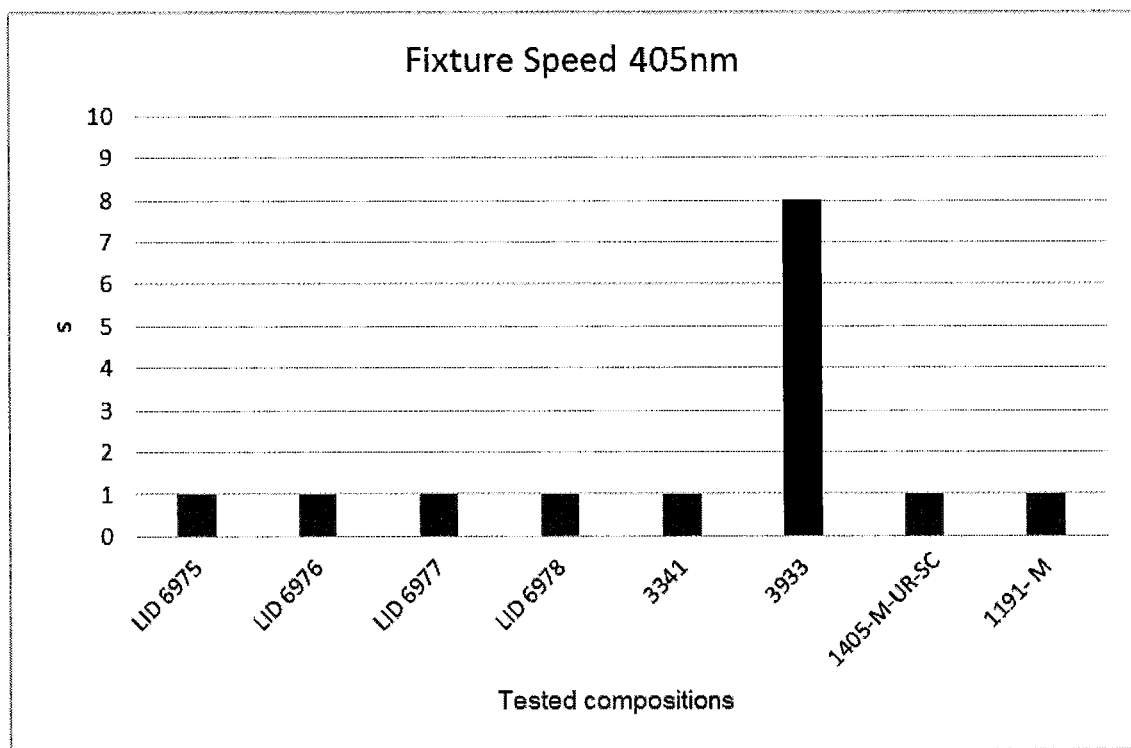
FIG. 3 is a bar chart depicting the fixture speeds (time in seconds, s) of the tested compositions at 405 nm. Good fixture times of less than one second on glass slides at 10 mW are seen for all of the compositions claimed in the current invention.
Figure 4:
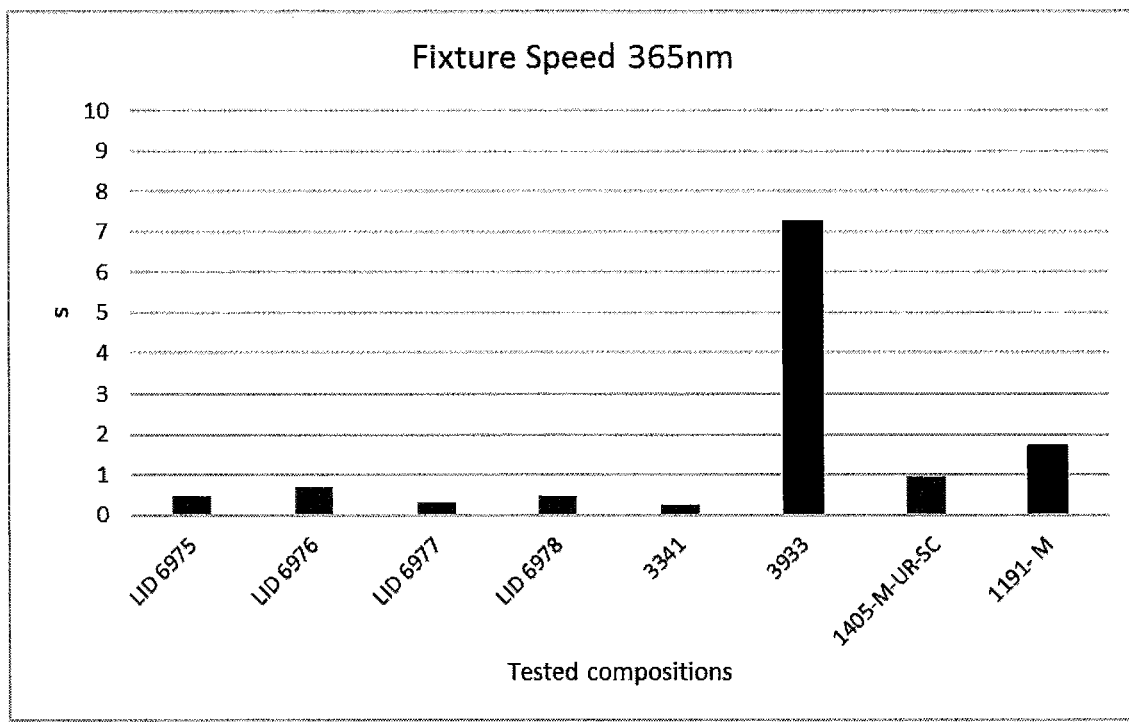
FIG. 4 is a bar chart depicting the fixture speeds (time in seconds) of the tested compositions at 365 nm. Good fixture times of less than one second on glass slides at 10 mW are seen for all of the compositions of the invention.

Fixture Time Test:

The rapidity of fixture was measured using glass microscopic slides, where fixture time (seconds) was defined as the time of exposure to actinic radiation required to develop a shear strength greater than 0.1 N/mm$^2$. The results obtained for the tested compositions, including controls are reported for 10 mW sources: LED flood array at 405 nm in FIG. 3; and UV-A radiation at 365 nm in FIG. 4.

Figure 5:
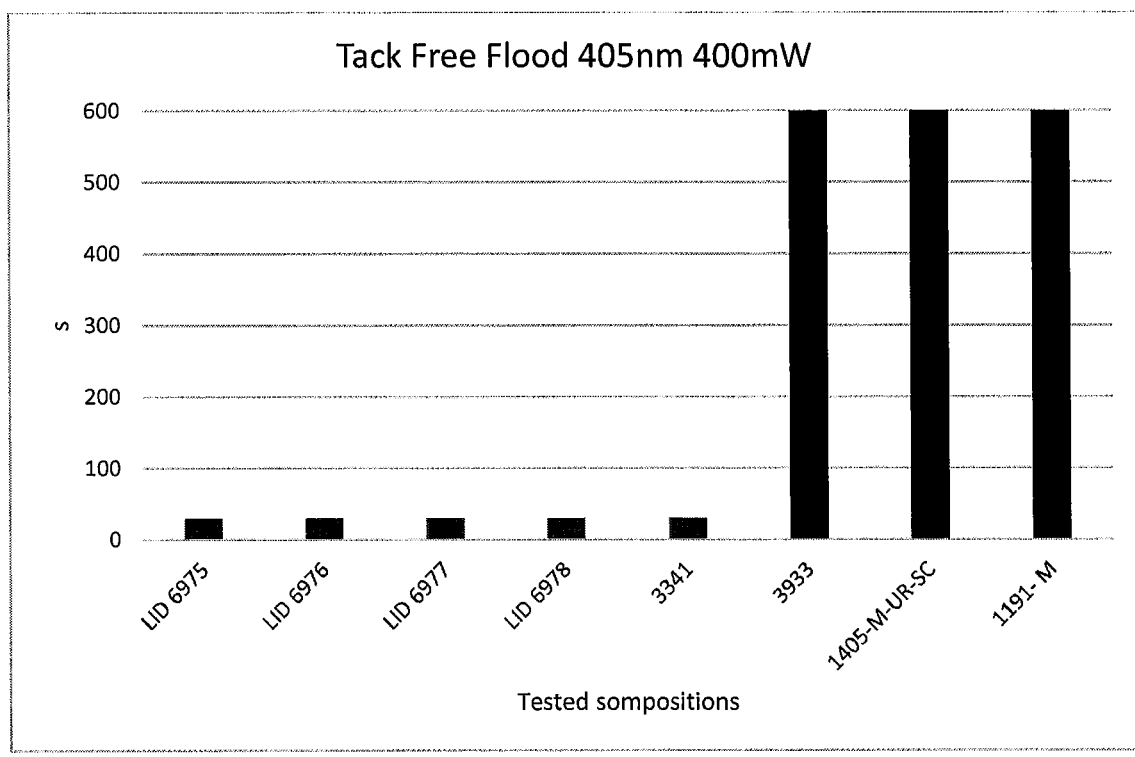
FIG. 5 is a bar chart depicting the tack-free cure at a depth of 1 mm on glass slides at low intensity 400 mW, on Flood 405 nm (≤30 s). No tack-free cure was observed for 3933, 1405-M-UR-SC, or 1191-M out to 10 mins.
Figure 6:
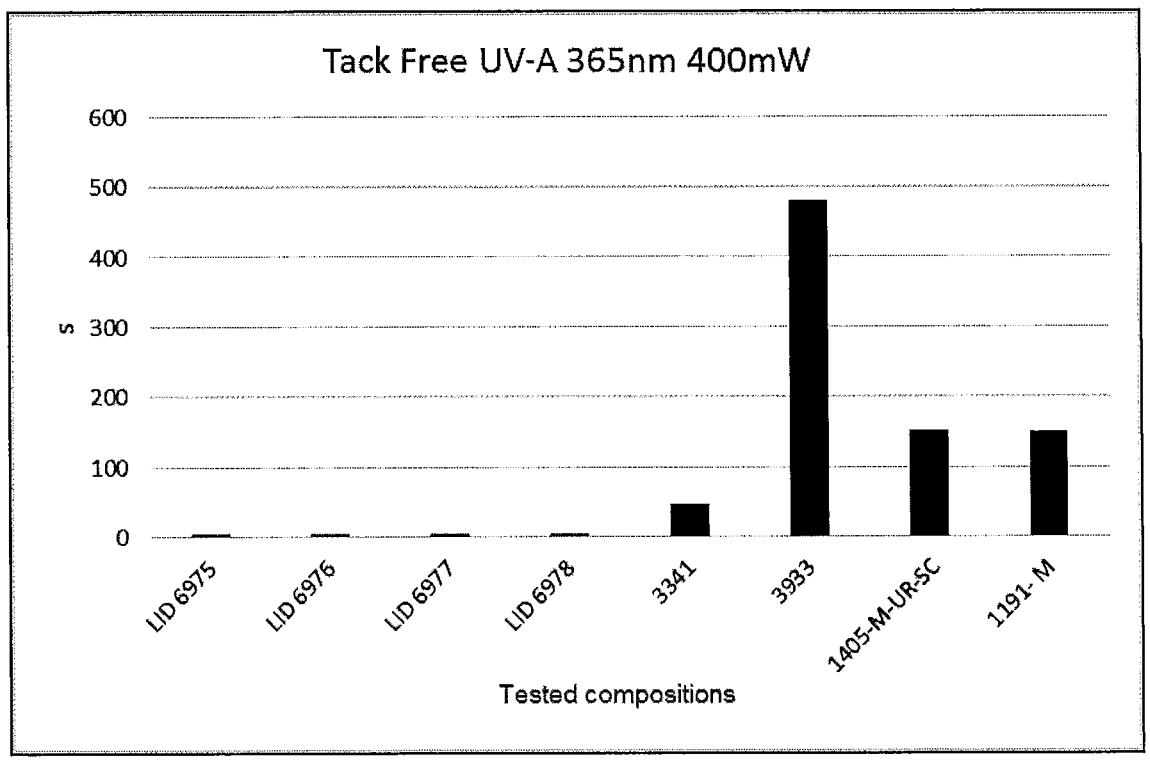
FIG. 6 is a bar chart depicting the tack-free cure at a depth of 1 mm on glass slides at low intensity 400 mW UV-A at 365 nm (<5 s).

Tack-Free Test:

A 1 mm tall sample of each tested composition, including the controls, was placed in a Loctite 405 nm flood array (an LED source of actinic radiation) and cured at 400 mW low light intensity. After curing, a light dusting of talcum powder was dusted onto the cured surface. The talcum powder was removed, if able, by lightly rubbing the surface with a clean absorbent paper towel such as a Kimwipe® or equivalent. Tack-free cure was considered to have been achieved when the talcum powder could be removed without altering the surface of the adhesive or causing the surface to become dull. A similar test was performed at 400 mW intensity using an LED source of 365 nm actinic radiation (UV-A). The results of these tests are reported in FIG. 5 and FIG. 6.

Figure 7:
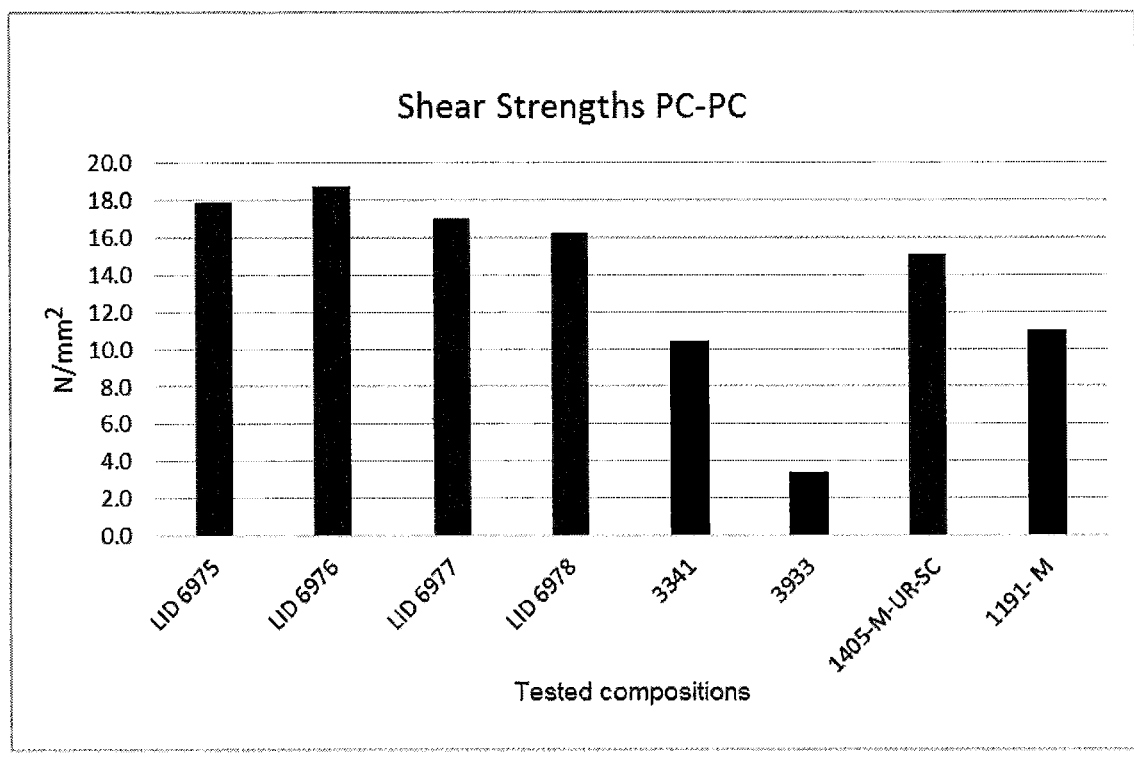
FIG. 7 is a bar chart depicting the shear strengths of the tested cured compositions, in a lap-shear test on polycarbonate to polycarbonate (PC-PC).
Figure 8:
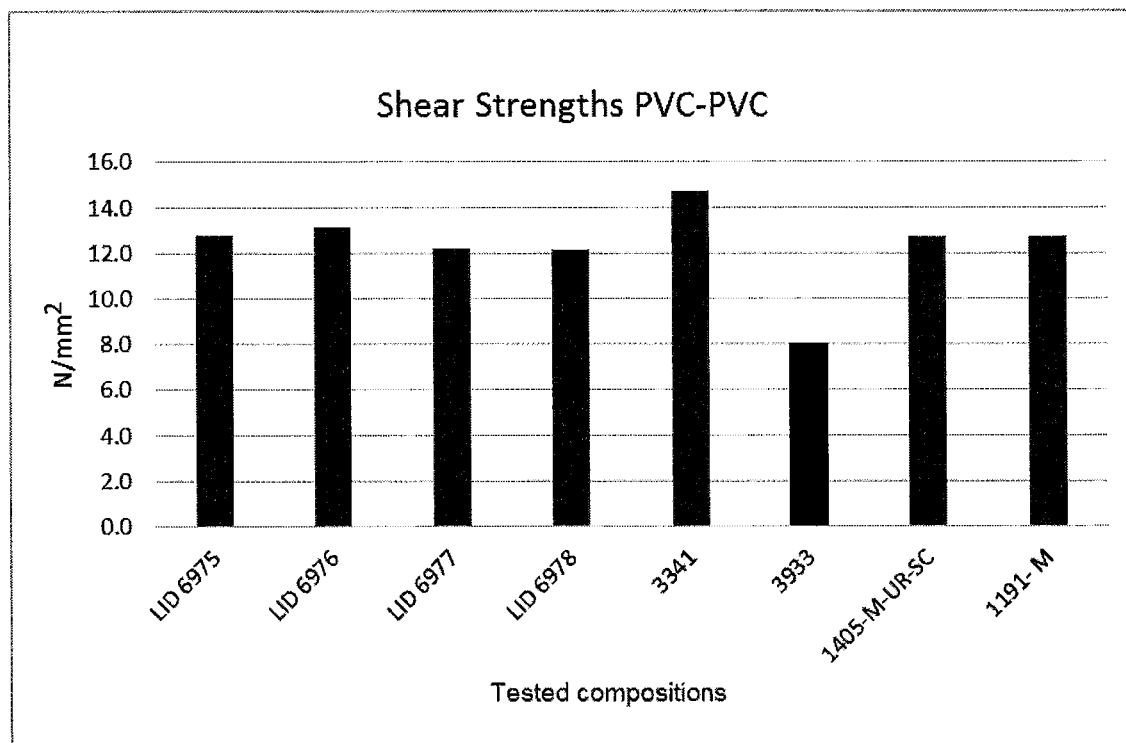
FIG. 8 is a bar chart depicting the shear strengths of the tested cured compositions, in a lap-shear test on polyvinylchloride to polyvinylchloride (PVC-PVC).
Figure 9:
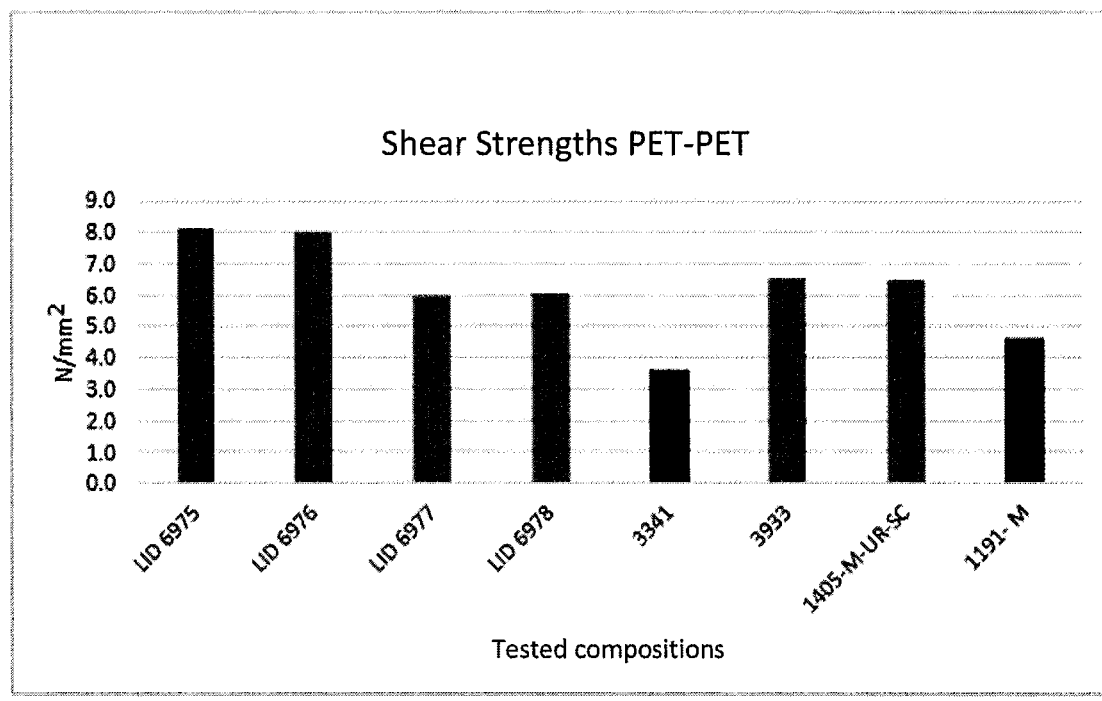
FIG. 9 is a bar chart depicting the shear strengths of the tested cured compositions, in a lap-shear test on polyethylene terephthalate to polyethylene terephthalate (PET-PET).
Figure 10:
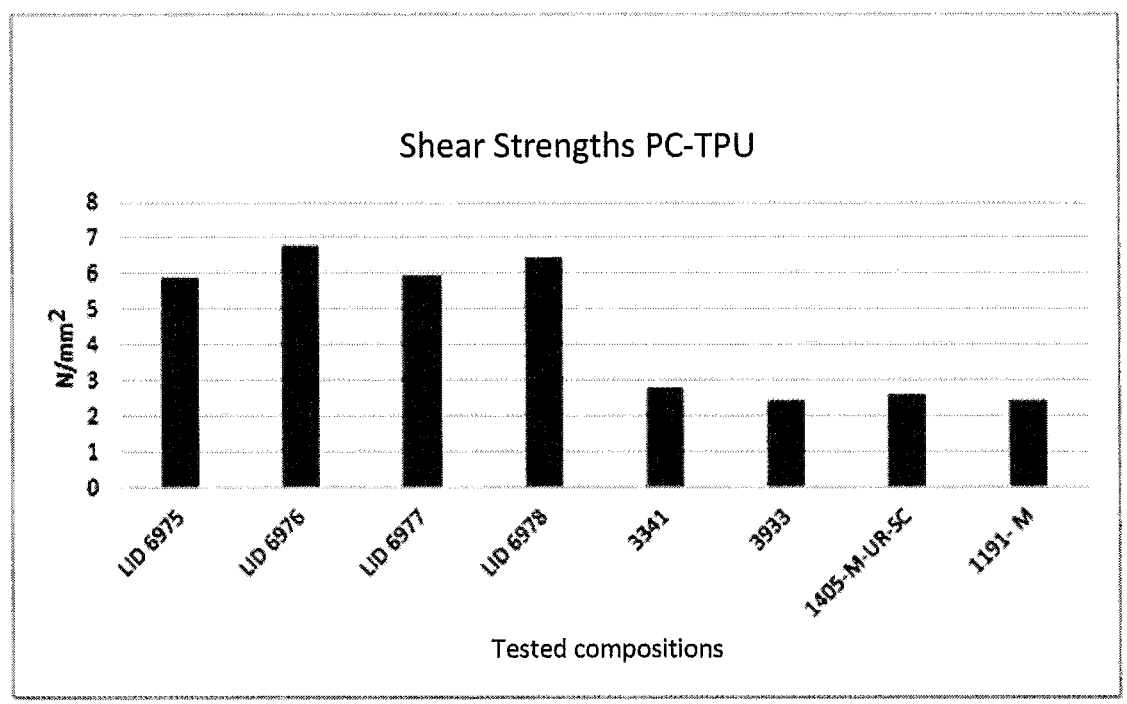
FIG. 10 is a bar chart depicting the shear strengths of the tested cured compositions, in a lap-shear test on polycarbonate to thermoplastic polyurethane (PC-TPU).
Figure 11:
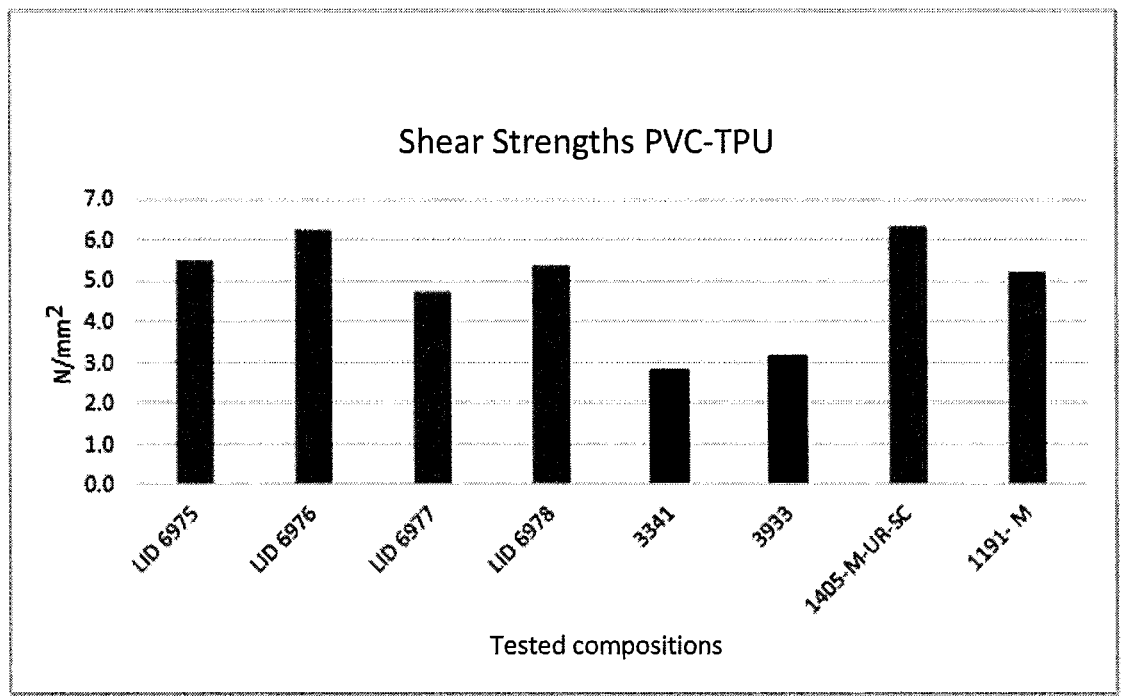
FIG. 11 is a bar chart depicting the shear strengths of the tested cured compositions, in a lap-shear test on polyvinylchloride to thermoplastic polyurethane (PVC-TPU).
Figure 12:
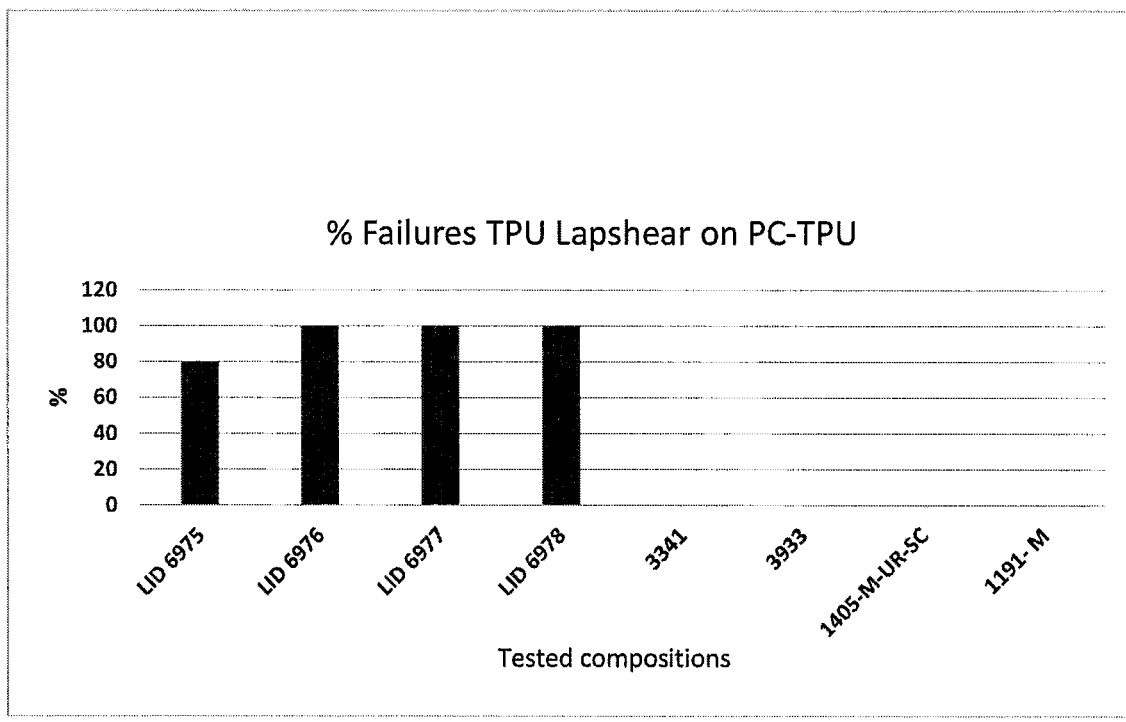
FIG. 12 is a bar chart depicting the percentage occurrence of lap shear substrate failure in lap-shear tests of the tested cured compositions on polycarbonate to thermoplastic polyurethane (PC-TPU). All of the prior art compositions exhibited failure modes involving debonding from the thermoplastic polyurethane. Accordingly, these prior art compositions produced no (that is, 0%) incidents of substrate failure and therefore no bars are visible on the chart for these prior art compositions. In contrast, in these tests, substrate failure was the typical mode of failure for compositions of the invention; that is, adhesive bonding remained intact while the substrate of the lap shear broke. This performance is indicative of strong bond strength by the compositions of the invention.

Lap-Shear Test:

Adhesive lap-shear bond strength was determined, following curing of the composition with actinic radiation, by stressing a single-overlap joint between rigid test adherends in shear by the application of a tensile force parallel to the bond area and to the major axis of the specimen. Tests were performed as set out in ISO 4587. Lap shears were overlapped by about 0.6 cm (one quarter of an inch). Tested substrates include PC-PC (FIG. 7), PVC-PVC (FIG. 8), PET-PET (FIG. 9), PC-TPU (FIG. 10), and PVC-TPU (FIG. 11). The term Substrate-failure refers to rupture of the substrate during a lap-shear test; a result indicative of exceptionally strong bonding. The percentage occurrence of substrate failure during lap-shear testing is depicted in FIG. 12, for the tested compositions using PC-TPU lap-shears.

Results of the tested compositions are reported in Table 1 and depicted in FIGS. 1-12.

The tested compositions of the invention (LID6975, LID6976, LID6977, LID6978) all exhibited the sought properties, as outlined herein and in the 'Target performance' column of Table 1.

TABLE 1

| Properties | Specific Performance Attribute/Testing | Target performance | Examples of Compositions of the Current Invention | | | | Commercially Available Photocurable Adhesive Compositions | | | |
|---|---|---|---|---|---|---|---|---|---|---|
| | | | LID6975 | LID6976 | LID6977 | LID6978 | Loctite 3341 | Loctite 3933 | Dymax 1405-M-UR-SC | Dymax 1191-M |
| Viscosity | Viscosity (mPa · s), at 25° C. | <500 mPa · s | 118.8 | 116.2 | 413.4 | 411.7 | 602.5 | 2127 | 685.9 | 948.8 |
| Flexibility | Elongation-at-break (%) | >130% | 182.2% | 175.0% | 169.5% | 181.5% | 153.6% | 178.8% | 150.0% | 115.0% |
| Fixture speed (time in seconds) | Fixture time 405 nm, 10 mW (s) | 1 s or less | 1 | 1 | 1 | 1 | 1 | 8 | 0.95 | 1.7 |
| | Fixture time 365 nm, 10 mW (s) | 1 s or less | 0.45 | 0.7 | 0.3 | 0.45 | 0.25 | 7.25 | 1 | 1 |
| Tack-Free time | Tack-Free 405 nm, 400 mW, (s) | <40 s | 30 | 30 | 30 | 30 | 30 | No tack-free out to 600 s | No tack-free out to 600 s | No tack-free out to 600 s |
| | Tack-Free 365 nm, 400 mW, (s) | <5 s | 3 | 3 | 3 | 3 | 45 | 480 | 150 | 150 |
| Strength (N/mm$^2$) | Shear strength PC-PC | >15 N/mm$^2$ | 17.9 | 18.8 | 17.1 | 16.2 | 10.4 | 3.4 | 15.1 | 11 |
| | Shear strength PC-TPU | >5 N/mm$^2$ | 5.9 | 6.8 | 5.9 | 6.4 | 2.8 | 2.4 | 2.6 | 2.4 |
| | Shear strength PET-PET | >5 N/mm$^2$ | 8.1 | 8.0 | 5.9 | 6.0 | 3.6 | 6.5 | 6.4 | 4.6 |
| | Shear strength PVC-PVC | >10 N/mm$^2$ | 12.8 | 13.1 | 12.2 | 12.2 | 14.7 | 8 | 12.7 | 12.7 |
| | Shear strength PVC-TPU | >4 N/mm$^2$ | 5.5 | 6.2 | 4.7 | 5.3 | 2.8 | 3.1 | 6.3 | 5.2 |
| | Substrate Failure, PC-TPU | >50% | 80% | 100% | 100% | 100% | 0% | 0% | 0% | 0% |

Shortcomings in State of the Art Compositions with Respect to the Sought after Properties 3341: This composition has a viscosity of 602.5 mPa·s; thus, it does not achieve the targeted viscosity value (<500 mPa·s). 3341 has a tack-free cure time of 45 s when treated with low intensity (400 mW) UV-A (365 nm); thus it does not meet the targeted performance (<5 s). The strength of 3341, as measured in lap-shear tests, is lower than the targeted value for certain plastics (PC-PC, PC-TPU, PET-PET, PVC-TPU). For PC-PC the shear strength of 3341 is 10.4 N/mm$^2$, which is lower than the targeted value (>15 N/mm$^2$). For PC-TPU the shear strength of 3341 is 2.8 N/mm$^2$, which is lower than the targeted value (>5 N/mm$^2$). For PET-PET the shear strength of 3341 is 3.6 N/mm$^2$, which is lower than the targeted value (>5 N/mm$^2$). Substrate-failure is not seen (0% occurrence) in lap-shear tests using 3341 on PC-TPU; the target performance value is >50%.

3933: This composition has a viscosity of 2127 mPa·s thus, it does not achieve the targeted viscosity value (<500 mPa·s). 3933 has a fixture time of 8 s when treated with 10 mW actinic radiation at 405 nm; thus, it does not meet the targeted performance (1 s or less). 3933 has a fixture time of 7.25 s when treated with 10 mW actinic radiation at 365 nm; thus, it does not meet the targeted performance (1 s or less). When treated with low intensity actinic radiation (400 mW LED light) at 405 nm, no tack-free cure is seen for 3933, out to 10 mins; thus, it does not meet the targeted performance (<40 s). Similarly, 3933 has a tack-free cure time of 480 s when treated with low intensity (400 mW) UV-A (365 nm); thus it does not meet the targeted performance (<5 s). The bond strength of 3933, as measured in lap-shear tests, is lower than the targeted value for certain plastics (PC-PC, PC-TPU, PVC-PVC, PVC-TPU). For PC-PC the shear strength of 3933 is 3.4 N/mm$^2$, which is lower than the targeted value (>15 N/mm$^2$). For PC-TPU the shear strength of 3933 is 2.4 N/mm$^2$, which is lower than the targeted value (>5 N/mm$^2$). For PVC-PVC the shear strength of 3933 is 8 N/mm$^2$, which is lower than the targeted value (>10 N/mm$^2$). For PVC-TPU the shear strength of 3933 is 3.1 N/mm$^2$, which is lower than the targeted value (>4 N/mm$^2$). Substrate-failure is not seen (0% occurrence) in lap-shear tests using 3933 on PC-TPU; the target performance value is >50%.

1405-M-UR-SC: This composition has a viscosity of 685.9 mPa·s, thus, it does not achieve the targeted viscosity value (<500 mPa·s). When treated with low intensity actinic radiation (400 mW LED light) at 405 nm, no tack-free cure is seen for 1405-M-UR-SC, out to 10 mins; thus, it does not meet the targeted performance (<40 s). Similarly, 1405-M-UR-SC has a tack-free cure time of 150 s when treated with low intensity (400 mW) UV-A (365 nm); thus it does not meet the targeted performance (<5 s). The strength of 1405-M-UR-SC, as measured in lap-shear tests on PC-TPU is 2.6 N/mm$^2$, which is lower than the targeted value (>5 N/mm$^2$). Substrate-failure is not seen (0% occurrence) in lap-shear tests using 1405-M-UR-SC on PC-TPU; the target performance value is >50%.

1191-M: This composition has a viscosity of 948.8 mPa·s, thus, it does not achieve the targeted viscosity value (<500 mPa·s). 1191-M has an elongation-at-break value of 115%, which does not meet the targeted performance (>130%). 1191-M has a fixture time of 1.7 s when treated with 10 mW actinic radiation at 405 nm; thus, it does not meet the targeted performance (1 s or less). When treated with low intensity actinic radiation (400 mW LED light) at 405 nm, no tack-free cure is seen for 1191-M, out to 10 mins; thus, it does not meet the targeted performance (<40 s). Similarly, 1191-M has a tack-free cure time of 150 s when treated with low intensity (400 mW) UV-A (365 nm); thus, it does not meet the targeted performance (<5 s). The strength of 1191-M, as measured in lap-shear tests, is lower than the targeted value for certain plastics (PC-PC, PC-TPU, PET-PET). For PC-PC the shear strength of 1191-M is 11 N/mm$^2$, which is lower than the targeted value (>15 N/mm$^2$). For PC-TPU the shear strength of 1191-M is 2.4 N/mm$^2$, which is lower than the targeted value (>5 N/mm$^2$). For PET-PET the shear strength of 1191-M is 4.6 N/mm$^2$, which is lower than the targeted value (>5 N/mm$^2$). Substrate-failure is not seen (0% occurrence) in lap-shear tests using 1191-M on PC-TPU; the target performance value is >50%.

None of 3341, 3933, 1405-M-UR-SC, and 1191-M meet all the targeted performance values for viscosity, tack-free cure time at either 405 nm or 365 nm subjected to actinic radiation at an intensity of 400 mW, and shear strength on PC-TPU as measured in lap-shear tests. The tested commercially available composition with the lowest viscosity value, 3341, still exceeded the target viscosity performance by about 20.5%. Furthermore, none of 3341, 3933, 1405-M-UR-SC, and 1191-M exhibit substrate failure during lap-shear tests on PC-TPU. In contrast, LID6975, LID6976, LID6977 and LID6978 meet the targeted performance for every tested property, or achieve a value superior to that which was targeted (Table 1).

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A photocurable (meth)acrylate composition comprising:
    tetrahydrofurfuryl acrylate;
    urethane acrylate resin;
    isobornyl acrylate;
    N,N-dimethylacrylamide; and
    a photoinitiator component, wherein the composition has a viscosity at 25° C. of less than about 550 mPa·s.

2. The photocurable (meth)acrylate composition according to claim 1, wherein the photocurable (meth)acrylate composition when photocured has an elongation-at-break value of greater than 130%.

3. The photocurable (meth)acrylate composition according to claim 1, wherein the photocurable (meth)acrylate composition has a fixture time of less than about 60 seconds, using actinic radiation from about 365 nm to 405 nm at an intensity of 500 mW or less.

4. The photocurable (meth)acrylate composition according to claim 1, wherein the photocurable (meth)acrylate composition achieves a tack-free surface cure in less than 40 seconds, when photocured for between 40 seconds and 0.05 seconds using actinic radiation from about 365 nm to 405 nm at an intensity of 500 mW or less.

5. The photocurable (meth)acrylate composition according to claim 1, wherein the photocurable (meth)acrylate composition when photocured has a shear strength as determined by ISO 4587 of greater than about 4 N/mm$^2$.

6. A photocurable (meth) acrylate composition comprising:
    tetrahydrofurfuryl acrylate;
    urethane acrylate resin;
    isobornyl acrylate;
    N,N-dimethylacrylamide; and
    a photoinitiator component, wherein the tetrahydrofurfuryl acrylate is present in an amount from about 5% to about 30% by weight based on the total weight of the composition.

7. The photocurable (meth)acrylate composition according to claim 6, wherein the urethane acrylate resin comprises oligomers having a number average molecular weight of from about 500 to about 100000 and/or having a mass average molar mass ($M_w$) of about 21000.

8. The photocurable (meth)acrylate composition according to claim 6, wherein the urethane acrylate resin is present in an amount from about 18% to about 45% by weight based on the total weight of the composition.

9. A photocurable (meth)acrylate composition comprising:
    tetrahydrofurfuryl acrylate;
    urethane acrylate resin;
    isobornyl acrylate;

N,N-dimethylacrylamide; and
a photoinitiator component, wherein the isobornyl acrylate is present in an amount from about 15% to about 32% by weight based on the total weight of the composition.

10. A photocurable (meth)acrylate composition comprising:
tetrahydrofurfuryl acrylate;
urethane acrylate resin;
isobornyl acrylate;
N,N-dimethylacrylamide; and
a photoinitiator component, wherein the N,N-dimethylacrylamide is present in an amount from about 18% to about 30% by weight based on the total weight of the composition.

11. A photocurable (meth)acrylate composition comprising:
tetrahydrofurfuryl acrylate;
urethane acrylate resin;
isobornyl acrylate;
N,N-dimethylacrylamide; and
a photoinitiator component, wherein the composition further comprises an epoxide-bearing organosilane, wherein the epoxide-bearing organosilane is present in an amount from about 0.2% to about 2% by weight based on the total weight of the composition.

12. The photocurable (meth)acrylate composition according to claim 11, wherein the epoxide-bearing organosilane is 3-glycidoxypropyltrimethoxysilane.

13. The photocurable (meth)acrylate composition according to claim 1, wherein the photoinitiator component is selected from ethyl(2,4,6 trimethylbenzoyl)phenylphosphinate, 1-hydroxycyclohexylphenylketone, (2,4,6-trimethylbenzoyl)diphenylphosphineoxide, oxy-phenyl-acetic acid 2-[2 oxo-2-phenyl-acetoxy-ethoxy]-ethyl ester, oxy-phenyl-acetic 2-[2-hydroxy-ethoxy]-ethyl ester, 2-hydroxy-2-methyl-1-phenyl-1-propanone, phosphine oxide phenyl bis (2,4,6-trimethyl benzoyl), iodonium(4-methylphenyl)[4-(2-methylpropyl) phenyl]-hexafluorophosphate(1-), or combinations thereof.

14. The photocurable (meth)acrylate composition according to claim 1, wherein the photoinitiator component is present in an amount from about 0.01% to about 6% by weight based on the total weight of the composition.

15. A photocurable (meth)acrylate composition comprising:
tetrahydrofurfuryl acrylate;
urethane acrylate resin;
isobornyl acrylate;
N,N-dimethylacrylamide; and
a photoinitiator component, wherein the composition further comprises a fluorescent agent, wherein the fluorescent agent is present from about 0.005% to about 0.5% by weight based on the total weight of the composition.

16. The photocurable (meth)acrylate composition according to claim 15, wherein the fluorescent agent is 2,5-thiophenediylbis(5-tert-butyl-1,3-benzoxazole).

17. The photocurable (meth)acrylate composition according to claim 15, wherein the fluorescent agent is a synthetic organic molecule with a fluorescence emission range from about 615 nm to about 640 nm.

18. A photocurable (meth)acrylate composition comprising:
(i) tetrahydrofurfuryl acrylate in an amount 9% to about 15% by weight based on the total weight of the composition;
(ii) urethane acrylate resin from about 34% to about 49% by weight based on the total weight of the composition;
(iii) isobornyl acrylate from about 23% to about 28% by weight based on the total weight of the composition;
(iv) N,N-dimethylacrylamide from about 24% to about 24.5% by weight based on the total weight of the composition; and
(v) a photoinitiator component; and wherein the composition optionally further comprises at least one of:
(vi) an epoxide-bearing organosilane, in an amount from about 0.9% to about 1.1% by weight based on the total weight of the composition; or
(vii) a fluorescent agent in an amount from about 0.08% to about 0.12% by weight based on the total weight of the composition.

19. A method of curing a photocurable (meth)acrylate composition comprising the steps of:
(i) applying a composition according to claim 7 to a first substrate; and
(ii) exposing the composition to light from an LED or other light source or other actinic radiation source, e-beam, or mercury arc, so as to cure the composition, wherein at least one substrate is a flexible UV transparent part.

20. A method of curing a photocurable (meth)acrylate composition comprising the steps of:
(i) applying a composition according to claim 6 to a first substrate; and
(ii) exposing the composition to light from an LED or other light source or other actinic radiation source, e-beam, or mercury arc, so as to cure the composition, wherein the light source emits light with a wavelength in the range from 200 to 600 nm.

21. A method of curing a photocurable (meth)acrylate composition comprising the steps of:
(i) applying a composition according to claim 6 to a first substrate; and
(ii) exposing the composition to light from an LED or other light source or other actinic radiation source, e-beam, or mercury arc, so as to cure the composition, wherein the exposure of the composition to the light from the light source or other actinic radiation source occurs for a time of less than about 50 seconds and results in a tack-free cure of the composition.

22. A method of curing a photocurable (meth)acrylate composition comprising the steps of:
(i) applying a composition according to claim 6 to a first substrate; and
(ii) exposing the composition to light from an LED or other light source or other actinic radiation source, e-beam, or mercury arc, so as to cure the composition, wherein the composition is used to bond the first substrate to a second substrate and exposure of the composition to the light from the light source or other actinic radiation source results in fixture, by curing of the composition, of the first substrate to the second substrate in a time of less than about 10 seconds.

23. A method of curing a photocurable (meth)acrylate composition comprising the steps of:
(i) applying a composition according to claim 6 to a first substrate; and
(ii) exposing the composition to light from an LED or other light source or other actinic radiation source, e-beam, or mercury arc, so as to cure the composition, wherein the LED is at most a 500 mW LED.

24. A method of curing a photocurable (meth)acrylate composition comprising the steps of:

(i) applying a composition according to claim 6 to a first substrate; and
(ii) exposing the composition to light from an LED or other light source or other actinic radiation source, e-beam, or mercury arc, so as to cure the composition, comprising bonding the first substrate to a second substrate, wherein the first substrate and the second substrate are each parts of medical devices and equipment and optionally thereafter sterilising the bonded assembly created by bonding the first substrate to the second substrate.

25. The method according to claim 24, wherein at least one of the first substrate and the second substrate is tubing.

26. The method according to claim 25, wherein the tubing is:
(i) for the transfer of medical fluids and gases;
(ii) in a form which is inserted into the body or for insertion within a tract;
(iii) part of an implantable device;
(iv) for connecting to a cannula which is for insertion into a;
(v) for connecting to a medical device or haemodialysis equipment; and
(vi) for use as a sheath.

27. A method of curing a photocurable (meth)acrylate composition comprising the steps of:
(i) applying a composition according to claim 6 to a first substrate; and
(ii) exposing the composition to light from an LED or other light source or other actinic radiation source, e-beam, or mercury arc, so as to cure the composition, wherein at least one of the first substrate and a second substrate are made of plastics material wherein at least one of the substrates is transparent to UV or visible light.

28. The method according to claim 27, wherein the plastics material is selected from polyvinyl chloride, polyethylene, polypropylene, polycarbonate, acrylonitrile butadiene styrene, polyethylene terephthalate and thermoplastic elastomers, and combinations thereof.

29. An assembly comprising a first substrate and a second substrate that are each parts of medical equipment and are bonded together utilising a composition according to claim 6 and optionally wherein the assembly is sterile.

* * * * *